United States Patent [19]
Grimaud

[11] Patent Number: 5,297,036
[45] Date of Patent: Mar. 22, 1994

[54] METHOD FOR THE CORRECTION OF THE MEASUREMENTS OF OPTICAL DENSITY MADE ON A RADIOGRAPHIC FILM

[75] Inventor: Michel Grimaud, Paris, France

[73] Assignee: General Electric CGR S.A., Issy Les Moulineaux, France

[21] Appl. No.: 748,813

[22] Filed: Aug. 22, 1991

[30] Foreign Application Priority Data

Aug. 31, 1990 [FR] France .................. 90 10859

[51] Int. Cl.⁵ ............................................. G06F 15/42
[52] U.S. Cl. ................................... 364/413.13; 382/6; 382/54
[58] Field of Search ............... 364/413.13, 413.22; 382/6, 54; 378/99, 100

[56] References Cited

U.S. PATENT DOCUMENTS

| | | | |
|---|---|---|---|
| 3,673,394 | 6/1972 | Hartmann | 364/578 |
| 4,356,398 | 10/1982 | Komaki et al. | 364/413.13 |
| 4,794,531 | 1/1988 | Morishita et al. | |
| 4,811,090 | 3/1989 | Khurana | |
| 4,991,092 | 2/1991 | Greensite | 364/413.13 |
| 5,124,913 | 6/1992 | Sezan et al. | 364/413.13 |

FOREIGN PATENT DOCUMENTS 2555003  5/1985  France .

Primary Examiner—Donald E. McElheny, Jr.
Attorney, Agent, or Firm—Nilles & Nilles

[57] ABSTRACT

To carry out an automatic processing operation on radiographic images in mammography, it is shown that it is possible to correct the harmful effects of the linearity defect of the characteristic curve of sensitivity of the radiographic film used for this radiograph by making a statistical study of the noise in this image. It is shown that this statistical study enables the correction elements to be deduced directly using a top hat transformation. The processing is then independent of any prior knowledge that might be had of the sensitivity of the film or of the conditions in which the examined radiographs were acquired as well as subsequently developed.

12 Claims, 6 Drawing Sheets

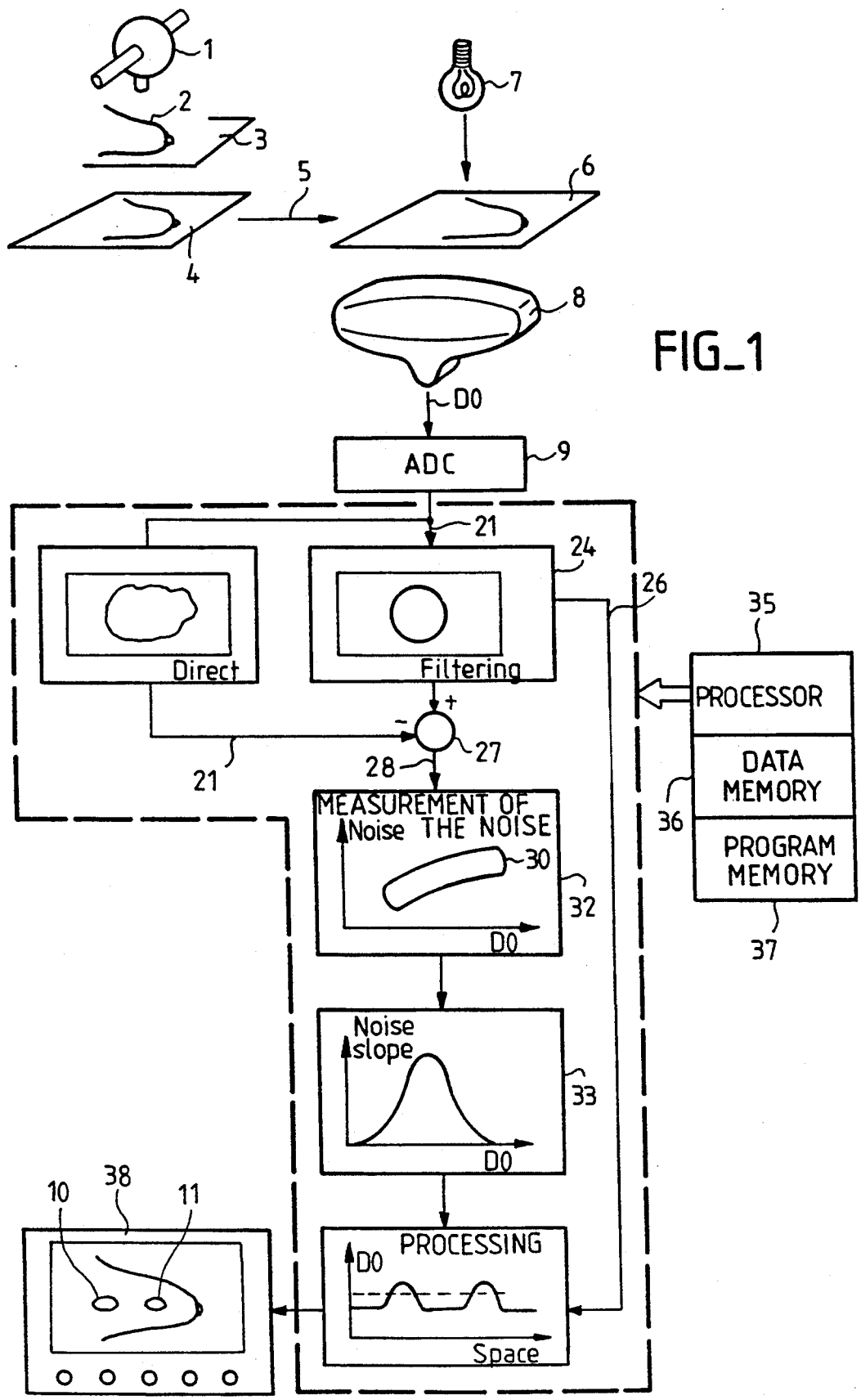
FIG_1

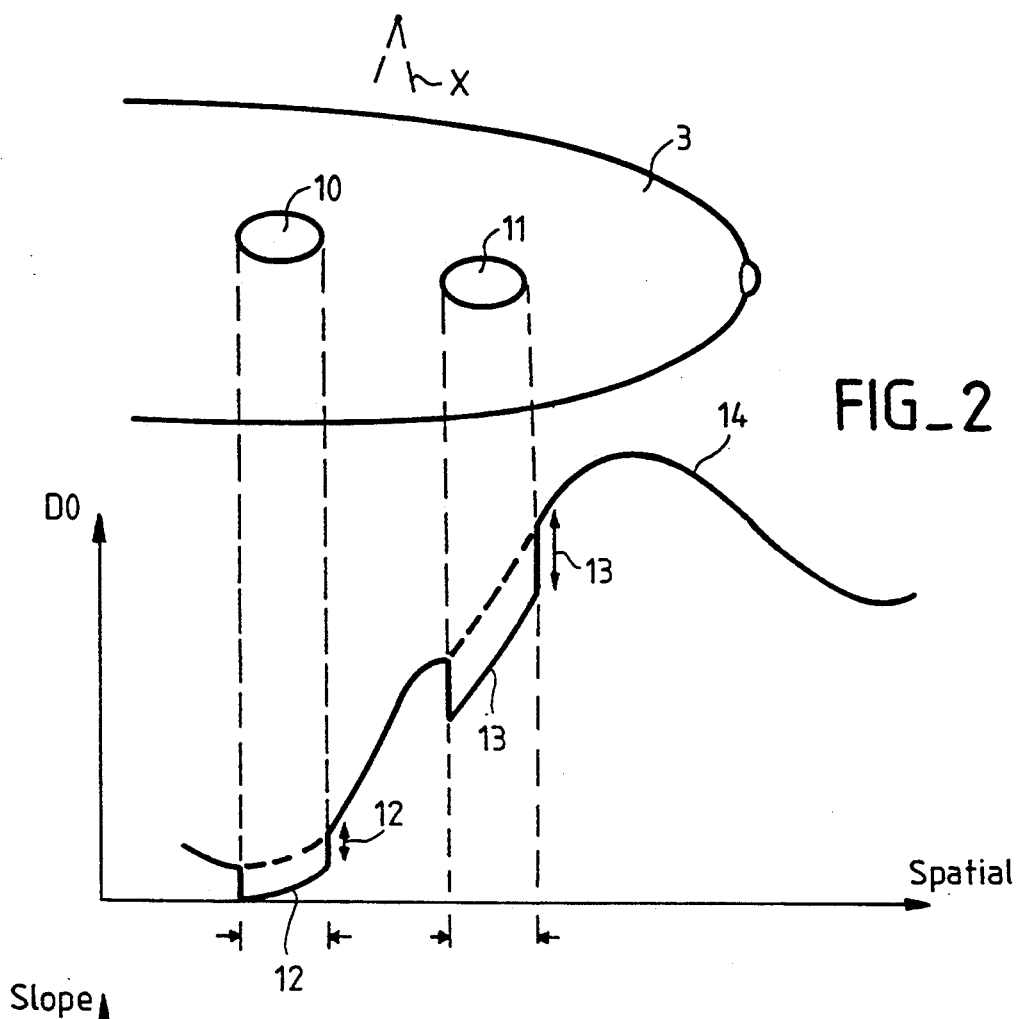
FIG_2
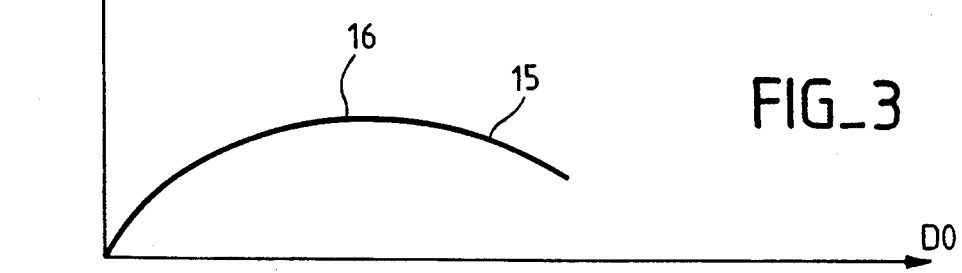
FIG_3
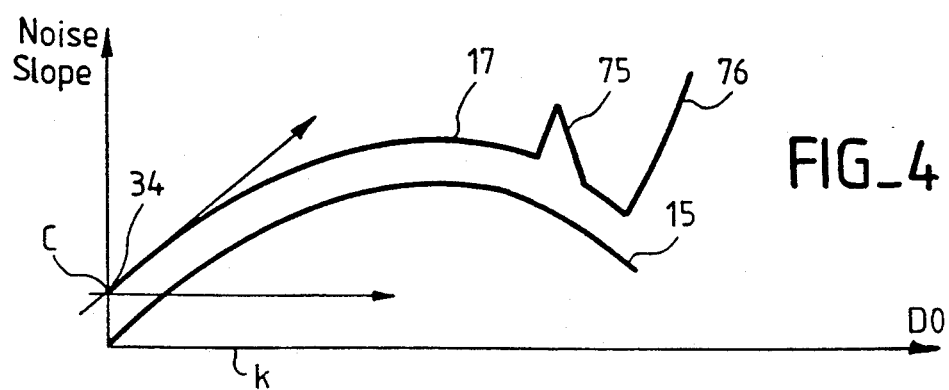
FIG_4

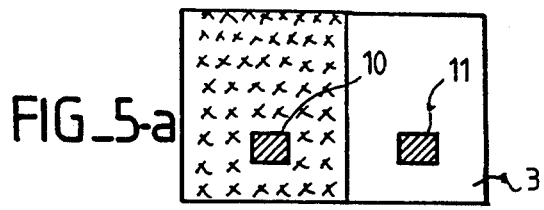
FIG_5-a
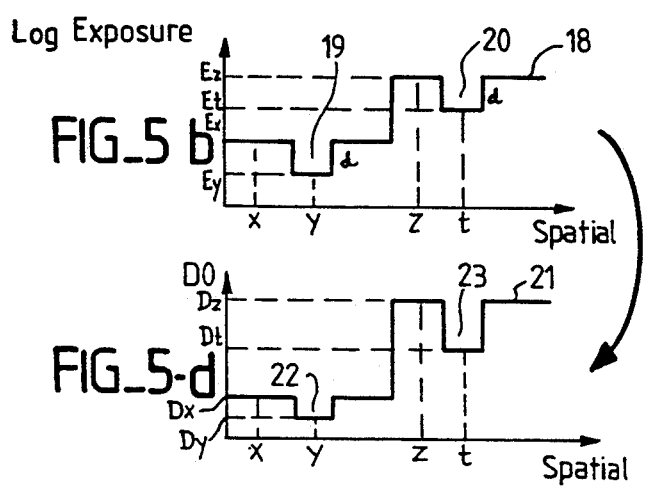
FIG_5 b
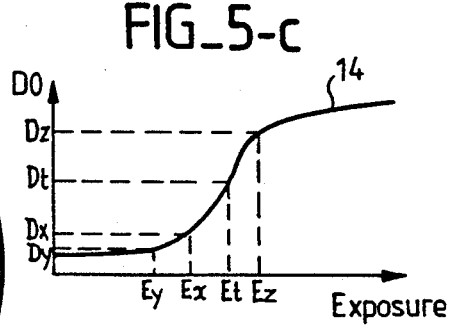
FIG_5-c
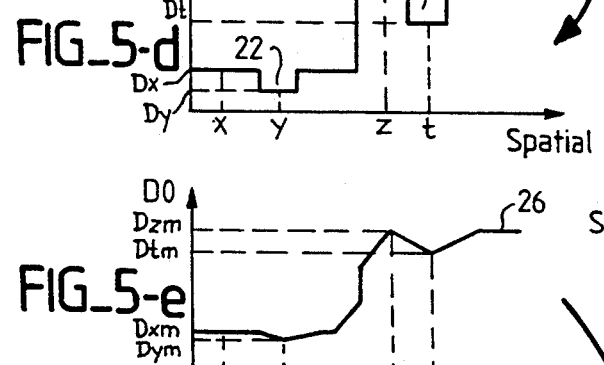
FIG_5-d
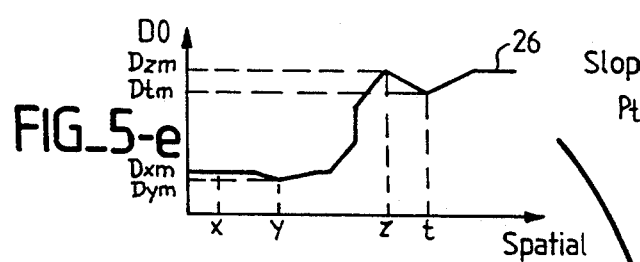
FIG_5-e
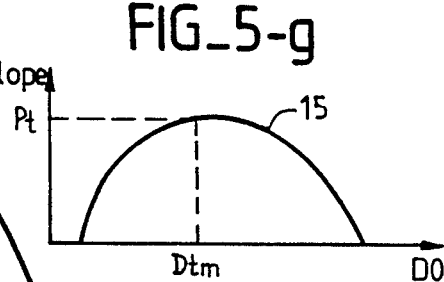
FIG_5-g
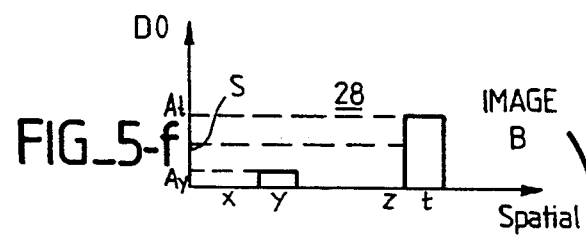
FIG_5-f
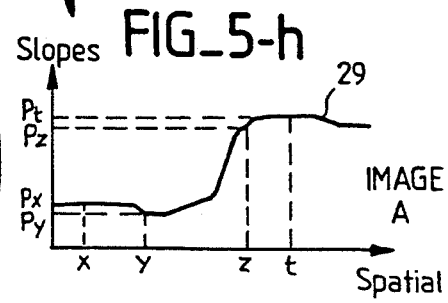
FIG_5-h
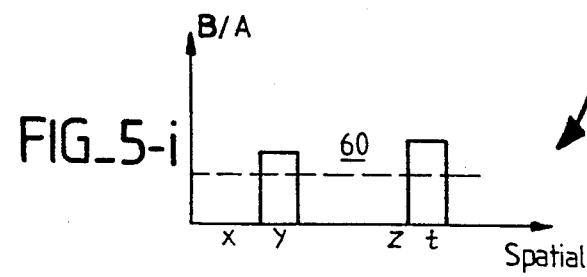
FIG_5-i

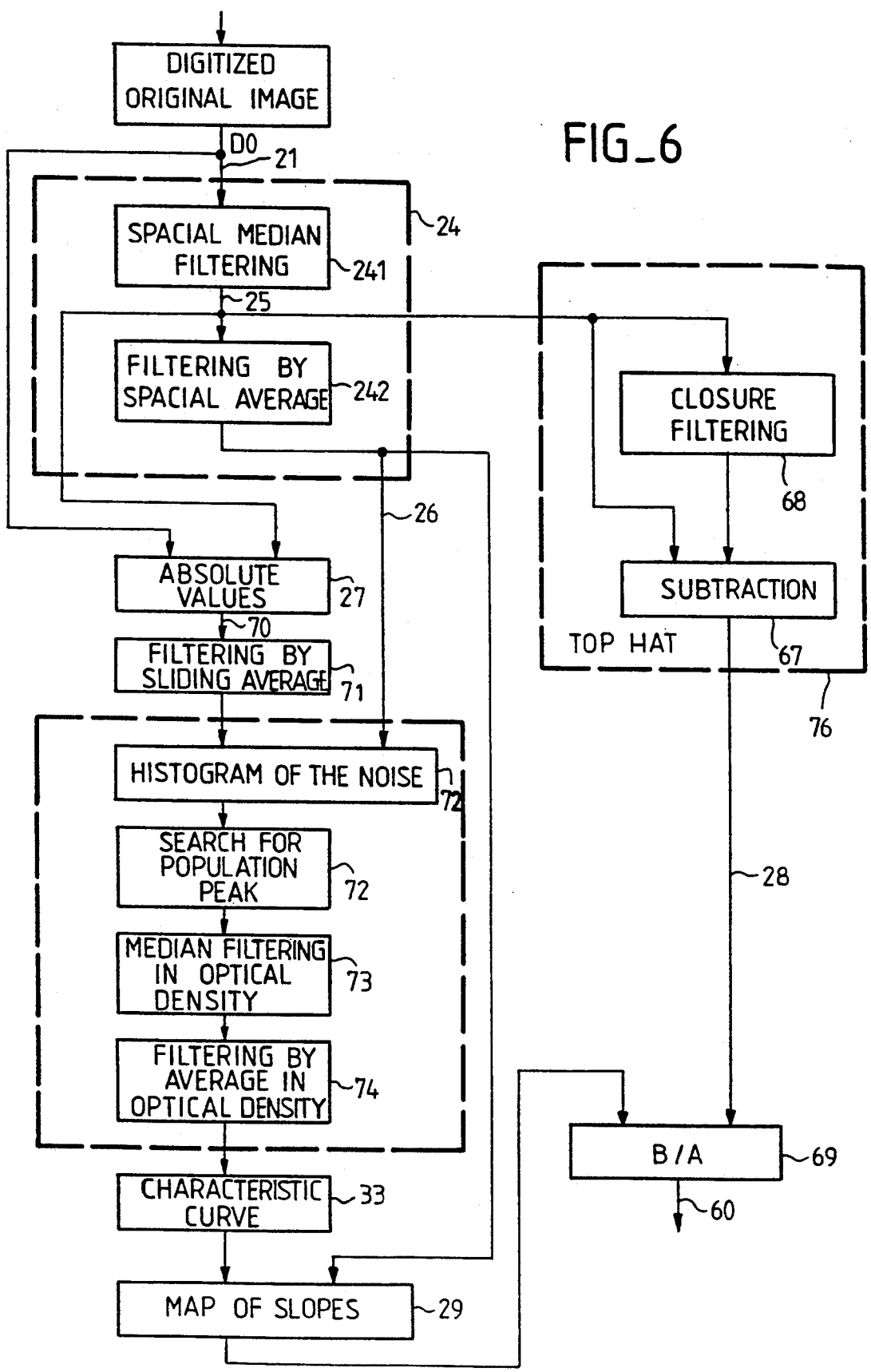

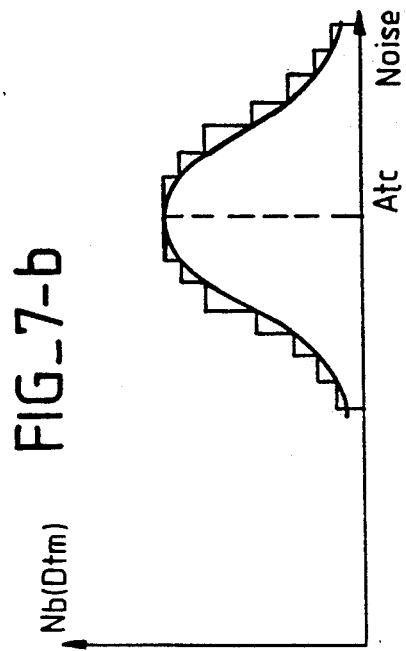
FIG_7-b
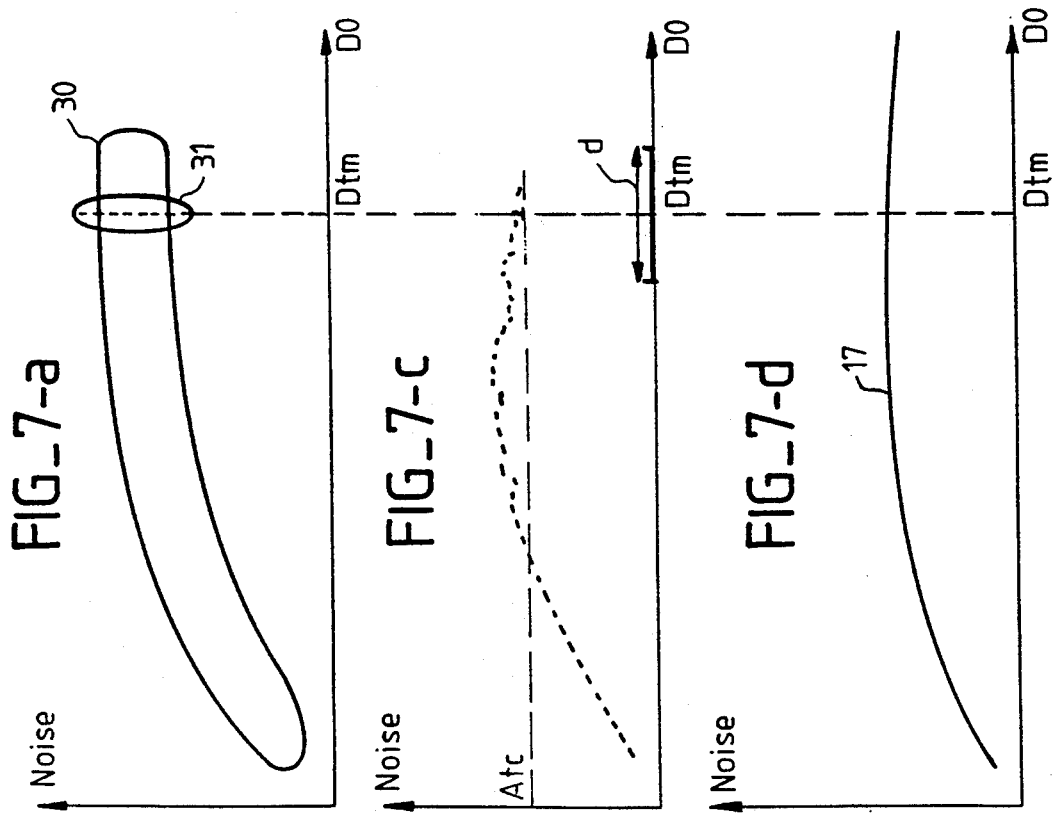
FIG_7-a
FIG_7-c
FIG_7-d

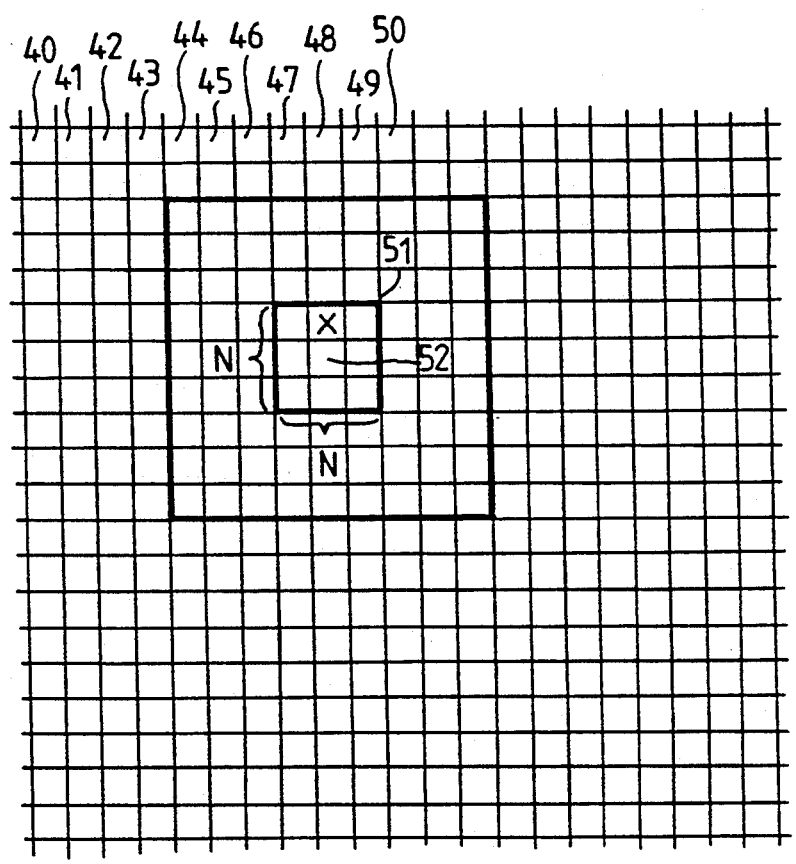
FIG_8

METHOD FOR THE CORRECTION OF THE MEASUREMENTS OF OPTICAL DENSITY MADE ON A RADIOGRAPHIC FILM

BACKGROUND OF THE INVENTION

1. Field of the Invention

An object of the invention is a method for the correction of the measurements of optical density made on a radiographic film. It can be applied, more particularly, to the field of medicine and, in this field it can be applied notably to mammography. The aim of the invention is to enable more reliable discrimination of small objects that can be characterized by their contrast, in also eliminating the disturbing effects due to the non-linearity of the characteristic curve of the sensitivity of the film.

2. Description of the Prior Art

Mammographic examinations are known in medicine. These examinations seek to reveal the microcalcifications which occur within patients' breasts and which may reveal the presence of cancerous tumors. The microcalcifications are small-sized (25 micrometers to some millimeters) calceous formations. The high density of the microcalcifications as compared with the surrounding tissues may enable them to be shown on the photographs despite their small size. It is also known that breast cancer affections can be successfully treated on condition that the treatment is done as early as possible after the appearance of the first signs. It is therefore important to detect the presence of these microcalcifications even though they are hardly visible.

A method for the computer-aided detection of microcalcifications is known, in particular from an article by Heang-Ping CHAN et al, "Computer-Aided Detection of Microcalcifications in Mammograms, Methodology and Preliminary Clinical Study" in the journal *Investigative Radiology*, September 1988, vol. 22, pp. 664 to 671. In this method, a radiological image, revealed by a radiographic film, is digitized in a known way. Then, on the digital signal got from this digitization, processing operations including, in particular, operations for comparison with a threshold, are carried out in order to make a statistical determination of the presence of clusters of microcalcifications in this radiograph.

One of the essential problems to be resolved then arises out of the fact that the sensitivity of the radiographic film is not linear as a function of the exposure that it has received. This is the integral of the X-radiation received by this film over the time during which this film has been subjected to radiation. The film bears a signal of optical density. The optical density is the blackening, which is pronounced in varying degrees, present in the radiograph after the photographic development of the film. It can be roughly assumed that the sensitivity of the film has three regions. In the first region, the sensitivity is low: the coefficient of correspondence of the variations in difference of exposure received and the associated differences in optical density is low. This first region corresponds to low values of exposure. In a second region, where the values of exposure are higher, the coefficient of correspondence is higher. In a third region, where the exposure is even higher, the coefficient of correspondence is again low.

The difficulty created by this situation in mammography is that the breast is formed by different tissues having different coefficients of attenuation. The variations in optical density are related to the presence and to the proportion of these different tissues. In those parts where the attenuation is the highest, the X-radiation will be more absorbed than in the parts were it is lower. As a consequence, the exposure received by the film directly on the parts where the attenuation is low will be greater than the exposure received directly on the parts where the attenuation is high.

It has been shown that microcalcifications of identical sizes prompt a variation in the exposure of the film that is the same irrespectively of the place in which these microcalcifications are located in the breast. In other words, when measured in terms of exposure, or more precisely in terms of the logarithm of the exposure, these microcalcifications show identical contrasts. Thus, owing to this defect of linearity in the curve of sensitivity, the microcalcifications located in the parts with high or low attenuation will be, to put it schematically, revealed by variations in the signal of optical density on the film that will be relatively smaller than those relating to microcalcifications that are located in those parts of the breast having mean attenuation (and that correspond to the exposed parts in an intermediate way: i.e. with the greatest sensitivity of the film).

To resolve this problem it has been discovered, in the invention, that the curve of sensitivity of the film has to be established in such a way that each value of optical density measured on the radiograph must be assigned an equivalent value corresponding to the logarithm of the exposure. This is achieved by a corrective function. In practice, this corrective function is the reverse of the function characterized by the characteristic curve of sensitivity of the film. In this way, the effects of this non-linearity are removed. It is therefore necessary to read the characteristic curve of sensitivity of the film.

There is also a known method by which, after the mammographic examination, phantoms of known radiological densities are placed on the film. An additional printing of the film is done by means of an apparatus called a sensitograph. The exposure of the parts of the film at the position of these phantoms is then known. The optical density values of the film, when it has been subsequently developed, may be assessed. Using these assessments of optical density and this knowledge of the exposure at the position of the phantoms, it is possible to analyze the radiograph by comparison. However, this technique has the drawback of being cumbersome to implement and, in practice, it is not implemented. What happens essentially is an instinctive human visual correction, for the practitioner then works on a radiograph and not on a digitized image. When this technique is not implemented, the correction is obtained by the experience of previous studies carried out by the practitioner on films of the same grain, and the same theoretical sensitivity, that have been subjected to similar exposures or are supposed to have been developed in the same way. Furthermore, this technique is applicable only if the characteristics of the shooting and the characteristics of the radiograph itself are known. This technique, therefore, cannot be applied to a radiograph of unknown origin or a radiograph that has no traces of phantoms; and yet this radiograph may be one that has to be used because it was taken at an earlier period and needs to be examined in order to assess the prior presence of these microcalcifications.

In the article cited, since the authors were unable to isolate the microcalcifications by a comparison with a single contrast value on the entire radiograph, they made use of an adaptive thresholding method. This is a standard technique in image analysis. The method consists in relating the thresholding value at one point to the information contained in the geographical vicinity of this point. In this specific case, they condition the thresholding by the value of the mean square deviation on the original image or on the spatially filtered image (the technical description is ambiguous) in a window with a size of 51 pixels by 51 pixels, i.e. a 5.1 mm×5.1 mm window since their images are digitized at 100 micrometers by 100 micrometers per pixel. These authors present an approach that provides for more efficient thresholding but does not seek to correct the effect of the variation in sensitivity. The difference between their approach and that of the invention is important from this point of view. The drawback of the method of this article is that the background of the image plays too great a role in the correction.

In an improvement, the present invention is aimed at overcoming these drawbacks in proposing a different technique by which the slope of the characteristic curve of a radiographic film is truly obtained even, in this case, without having any special prior information on the type of film, its conditions of exposure or its conditions of development. No presence of phantoms is necessary, in principle, for the invention. It has been discovered, in the invention, that the noise present on the film could enable an estimation of the characteristic curve of sensitivity of the film which represents the transfer function between the luminance of the X-photons that have imprinted the film and the blackening of the film resulting from this imprinting. The noise constitutes an exploratory phenomenon, at every dot of the film, of the sensitivity of the film at the place where this phenomenon occurs. It therefore suffices to measure the revealing of this noise. The characteristic curve is deduced therefrom.

There is a known method, described in an article by G. T. Barnes and D. P. Chakraborty, "Radiographic Mottle and Patient Exposure in Mammography" in the journal *Radiology*, Vol. 145, No. 3, pages 815–821, December 1982, in which the characteristic curve is related in analytical form to the noise measured in the image. But the conclusion drawn therefrom is that the exposure of the apparatus to X-rays must be optimized. This is not possible when dealing with acquired radiographs. Above all, this does not teach us how to compute the characteristic curve itself but, on the contrary, assumes that it is known.

SUMMARY OF THE INVENTION

An object of the invention is a method for correcting the measurement of the values of optical density, this measurement being done on a radiographic film, wherein:

an image of a radiographed object is revealed on a radiographic film and a value of optical density is measured for each dot of the film, this measurement leading to a signal of optical density of the radiographed image, wherein an estimation is made, for each level of optical density, of the slope of the characteristic curve of the transfer function made by the film, this characteristic curve establishing the correspondence between the radiographic exposure that the film has received and the optical density resulting therefrom, the map of the slopes of this characteristic curve is prepared, dot of the film by dot of the film, in assigning, to each dot of the image, a slope value of this curve, this slope value being a function of this curve and of the value of optical density at this dot, and the measurement of optical density is corrected at each dot as a function of the value of optical density at this dot and of the slope of the characteristic curve at this dot.

Furthermore, in one improvement, for each optical density level, an estimator of noise of the optical density signal is prepared, and the slope of the characteristic curve is deduced from this estimator.

BRIEF DESCRIPTION OF THE DRAWINGS

The invention shall be understood more clearly from the following description and from the appended figures. These figures are given purely as an indication and in no way restrict the scope of the invention. Of these figures:

FIG. 1 shows a schematic view of a device that can be used to implement the method of the invention;

FIG. 2 shows the shape of the optical density signal measured;

FIGS. 3 and 4 respectively show the slope of the characteristic curve of the film and its identification with the measurement of the noise, enabling an implementation of the invention;

FIGS. 5a to 5i are graphs representing the physical effects implemented in the invention;

FIG. 6 is a flow chart of the processing operation according to the invention;

FIGS. 7a to 7d show processing operations performed on noise measurements to enable the computation of the characteristic curve;

FIG. 8 is a diagram that enables an understanding of the signal processing operations carried out in the invention.

DETAILED DESCRIPTION OF THE INVENTION

FIG. 1 shows a device that can be used for the implementation of the method according to the invention. It shows a radiograph, taken by means of an X-ray tube 1, of a breast 2 placed on a breast-holder tray 3 with a view to imprinting a photosensitive film 4 located beneath the plate 3. After a standard type of chemical processing 5, the radiographic film 4 is developed into a radiograph 6. This radiograph is observed in a known way so as to be digitized.

The principle of the digitization consists in illuminating the radiograph 6 with a light source 7 and in observing the image of optical density, shown by the radiograph 6, by means of a photoreceiver 8. The signal DO, delivered by the photoreceiver 8, which is a signal that changes in time as a function of the examination of the lines of the image, is digitized in an analog-digital converter 9. The measurement, for each dot of the radiograph 6, of an optical density value may therefore be considered to be done by the photoreceiver 8. The optical density signal of the radiographed image, especially when it is digitized, may be considered to be the one emerging from the analog-digital converter 9.

Hereinafter, we shall show the physical effects of the processing operations to be performed on the digital signal (which itself is also referenced DO) delivered by the converter 9. It is, however, understood that the processing operations are done in a computer 35-37 that processes digitized information elements, normally encoded in binary form, corresponding to these images as a function of a program that shall be explained hereinafter. The image produced after processing may be shown on a monitor 38.

FIG. 2 gives a schematic view, beneath the irradiated breast 3, of the consequences of the variation in sensitivity of the film as a function of the nature of the exposure. The curve of FIG. 2 shows, for an image line of the radiograph 6, the signal 14 of measured optical density DO, as a function of the spatial x-axis value of a point measured on this line. This signal 14 has a profile that varies as a function of the coefficient of attenuation of the interposed tissues. Two microcalcifications 10 and 11, assumed to be exactly identical, prompt different variations 12 and 13 respectively of the signal of optical density on the radiograph 6. These different variations of the signal of optical density are due to different sensitivities of the film at the place where they are revealed. These variations in sensitivity are caused mainly by the different composition of the tissues above and beneath the microcalcifications 10 and 11.

FIG. 3 shows the curve 15 of the slope of the characteristic curve of sensitivity of the film. This slope 15 has a tip 16 corresponding to the place on the curve of sensitivity where this curve is at its steepest. In the invention, it has been discovered that, if the noise is measured, it is possible to choose a noise estimator proper to the radiograph 6, the characteristic curve 17 (FIG. 4) of which is quite comparable to the slope of the characteristic curve 15 of the radiograph 6. These two curves are deduced from each other by an additive constant C. The method of computing the value of this additive constant C shall be shown further below. Hence, in the invention, an assessment is made of the slope of the characteristic curve of the transfer function achieved by the film in preparing, for each level of optical density DO, a noise estimator of this signal of optical density.

FIGS. 5a to 5i give a schematic view of the steps of the method according to the invention. In these steps, the breast 3 and the microcalcifications 10 and 11 are represented by rectangular surfaces. These rectangular surfaces lead schematically to pulsed signals of optical density. FIG. 5b shows, for the density of the tissues of the breast of FIG. 5a, the different exposures to which the film 4 is subjected at different spatial x-axis values x, y, z, t. It is observed that the microcalcifications 10 and are echoed, in the exposure signal 18 shown, by two negative square-wave pulses 19 and 20 of the same height. By contrast (FIG. 5c) owing to the existence of the characteristic curve 14 of the film 4, the optical densities that can be seen on the radiograph 6 lead to a signal of optical density 21, (FIG. 5d) having two negative square-wave pulses, respectively 22 and 23, the essential characteristic of which is that they have different heights.

They therefore correspond to accidents of the same nature and are echoed, in the signal, in different forms. The image said to be original in terms of optical density, of FIG. 5d, may be converted by a spatial mediam filtering operation 241 followed by a spatial averaging operation 242. The spatial median filtering operation 241 essentially consists in the assigning, for each x-axis value of the curve 21, of another signal of optical density equal to the intermediate value of a list of values, arranged in rising order, of optical density DO measured for dots neighboring the dot studied. Rather than the intermediate value, it is also possible to take the value corresponding to the first or last quartile or, again, to any other subdivision. This median filtering converts the signal of the curve 21 into another signal 25. The spatial averaging operation 242 consists in the assigning, for each x-axis value of this other curve, of a new signal 26 of optical density equal to the mean of these other signals of the optical densities previously obtained at spatial locations in the vicinity of that of this x-axis value. The neighborhood of the spatial mean of the filter 242 is typically a 20×20 pixel neighborhood. This comprehensive operation, which is done in a filter 24 (FIG. 1), leads to a smoother shape 26 of the image of the contours of the breast 3. The filtered signal 26 is shown in FIG. 5e.

By carrying out the subtraction, in a subtractor 67, of the signal 25 filtered by the median filter 241 and of this signal 25 filtered by a filter 68 carrying out a closing operation, it is possible to obtain an signal 28 of optical density of the contrast of the microcalcifications. This closing filtration 68 shall be explained further below. The signal 28 is shown in FIG. 5f. Without the processing operation of the invention, it is seen that the comparison of the signal 28 with a threshold value S can be used to automatically reveal only the microcalcification 11: the insufficiently revealed microcalcification 10 passes unnoticed. With the invention, the signal 28 is modified in such a way that the threshold S can be compared homogeneously with the square-wave pulses corresponding to the microcalcifications 10 and 11.

In accordance with what has been stated here above, a slope of the characteristic curve is determined as a function of the sensitivity of the film expressed in optical density (FIG. 5g). It is extracted from the image noise. Then, the map 29 of the slopes at each dot of the image is prepared (FIG. 5h). To prepare the map 29, the following procedure is preferably carried out. For a given x-axis value of a dot, for example the x-axis value t, an associated optical density value Dtm is determined on a curve representing the phenomenon, for example the curve 26. A slope Pt, associated with the x-axis value Dtm is then determined on the curve of the slopes of FIG. 5g. The map 29 of the slopes is then prepared in associating, with the spatial x-axis value t, a y-axis value Pt deduced from the curve 15 (FIG. 5g) as corresponding to the x-axis value Dtm. It is also possible to prepare the map 29 of the slopes from the original image that has undergone only the median filtering or even from the original unfiltered image (curve 21, FIG. 5d).

The map 29 of the slopes is called the image A. The curve 28 obtained dot by dot at the output of the subtractor 67 is called the image B. The image 60, is then prepared with a correction B/A in an operation 69 (FIG. 5i) by combining the image B and the image A in such a way that, to each x-axis value common to these two images, there is assigned a y-axis value equal to the ratio of the assigned y-axis values in each of these two images.

The signal 60 enables the automatic detection of the microcalcifications by comparison with the threshold S, or by comparison with a threshold taking account of the correction itself if this correction is not standardized.

The method thus described with reference to figures 5a to 5i is the method of the invention. It is improved by a step consisting in the preparation of the curve 15 of the slopes from a noise estimator. The principle of the preparation of this noise estimator shall be explained with reference to FIGS. 6 and 7a to 7e. This estimator is prepared chiefly from a signal 70 available at output of a subtractor 27. The subtraction signals 70 are read for each of the lines of the image on the radiograph 6. These signals 70 are rectified so that only their absolute value is considered. This is why the subtractor 27 is called an absolute value subtractor. It will be noted that, in practical terms, in digital processing, this operation of taking the absolute values into account is a simple one. For, the digital subtraction of two signals leads to a digital result associated with a sign bit. In the present case it is enough, quite simply, to refrain from taking the sign bit into account. The statistical population studied therefore includes a set of pairs of values. The values of these pairs concern, firstly, the absolute values of the differences in optical densities and, secondly, the spatial addresses where these absolute values have been read. Rather than make direct use of the signal 70, it is preferred, in order to homogenize the noises on a small scale, to carry out a filtration 71, by sliding average. Thus, for 50 micrometer×50 micrometer pixels, the average of the absolute values of the pixels of the window is assigned to the central pixel of a 10 pixel×10 pixel window. The signal of absolute values, whether filtered or not, represents the noise alone since the object of the median filtering 241 was to eliminate this noise from the image signal. By subtraction with this image signal, the noise therefore appears alone.

The curve 26 will then be preferably used (in practice another curve could be used) to retain a correspondence between a spatial address and a filtered optical density value. FIG. 6 thus shows that the absolute values are obtained by subtraction of the original values from the original values filtered by the median filter only. Thus, with the address t seen here above, there is associated an absolute value At. On the curve 26, with the same address t, there had been associated an optical density, filtered by median filter and by averaging, with a value Dtm. A noise histogram is then prepared in an operation 72. The statistical population concerned is the population constituted by the pairs Dtm-At relating to a same spatial address t. This statistical population is shown on a graph (FIG. 7a). The absolute values At are shown on the y-axis as representing the noise. The optical densities filtered by the median filter and the averaging operation are shown on the x-axis. This task is performed for all the image dots of the radiograph 6. In practice, the operation could be limited to a smaller proportion of these numbers of image dots. This, however, would have the effect of making the subsequent statistical computations less reliable.

The essential feature of the improvement of the invention lies in the fact that the events of the statistical population are then distributed, in the graph of FIG. 7a, in a cloud 30 having substantially the shape of the slope of the characteristic curve 15 of the sensitivity of the film. Besides, this is what has led to the discovery of the invention. A set 31 of possible values of At is then observed, in taking up the above example, for a mean optical density Dtm. For, the value Dtm has been obtained several times and, at each time, values At that have no reason to be identical have been obtained.

A closer look was taken at the statistical distribution of these different values At of noise distributed in a certain number of ranges. It was then realized that the number N of occurrences in each range of values At had a bell shape, shown in FIG. 7b, on either side of a peak value Atc. FIG. 7b shows, for the optical density Dtm, the different possible values of At on the x-axis and the number Nb of events of the population, located at this value, on the y-axis. At a step 72 then, the cloud 30 of FIG. 7a is replaced by a curve represented by FIG. 7c in which, to each x-axis value Dtm, there is assigned a y-axis value corresponding to the population peak of FIG. 7b.

It is seen that the curve of the FIG. 7c is not a smooth curve. To use an acceptable curve, the non-continuous sequence of the points of the curve of FIG. 7c is then converted by a median filtering 73 followed by an averaging operation 74, both taken in a neighborhood measured along the axis of the optical densities. In a simple example with the median filter 73, at each x-axis position Dtm, the value Atc found is replaced by another value Atm equal to the median value of a set of values found on a segment d about Dtm. Here too, it is possible to choose another type of filtering. It is important, however, that this filtering be done as a function of a neighborhood measured along the axis of the optical densities. Then these other values Atm, filtered in a median way, are replaced by new values Atm obtained by the averaging of the values Atm found at x-axis positions neighboring the x-axis position Dtm and also located on a segment with a length d centered on Dtm. However, it is not necessary to take the same d twice. In the invention, d is equal to 5, the maximum value of Dtm being equal to 100. This operation is summarized at 32 in FIG. 6. The result of this processing operation can be seen in the form of the curve 17 in FIGS. 7d and 4.

The operation 32 for measuring the noise curve 17 is followed by an operation 33, which is a priori not necessarily an a priori operation, during which the constant C, used to measure the offset between the measured curve 17 and the true curve 15, is computed. This operation is not necessary since, in a downgraded application of the method, it is possible to overlook the computation of C. The slope of the real characteristic curve 15 is theoretically null at the starting point of the optical densities. Unfortunately, for an ordinary radiograph, the value of the noise at the starting point is not known. This value will therefore be estimated in assuming that, for the low values of optical density, the curve representing the noise estimator can be likened to a straight line. Using a numerical method of linear regression, a computation is then done of the ordinate of the point of intersection of the curve 17 with the y-axis. To this end, a cumulated histogram of the original image is made. A search is then made for the two gray levels, the values of which, in the cumulated histogram, are respectively 1% and 5% of the total number of pixels in the image. All that is kept then, from the noise function, is the interval between these two values. Then, using the least mean squares method, a search is made for the straight line approximating this reduced noise function. Let $Y_{est}=ax+b$ be the equation of this straight line. We have a set of couples $(x_i, y_i)$ where $x_i$ represents a gray level belonging to the above-defined interval and $y_i$ represents the noise level corresponding to this gray level. The least squares method seeks to minimize the quantity:

$$\Sigma_i(Y_{est}(x_i)-Y_i)^2=\Sigma_i(ax_i+b-Y_i)^2 \tag{1}$$

Minimizing this quantity amounts to cancelling the first derivatives of (1) with respect to a and b or, again, to resolve the following system of equations:

$$\Sigma_i(ax_i+b-Y_i)=0$$

$$\Sigma_i x_i(ax_i+b-Y_i)=0$$

This system of two equations with two unknowns makes it possible to find the value of the coefficients a and b. b is then the value of the subtractive constant C connecting the noise estimator and the slope of the characteristic curve.

The curve 17 has artifacts 75 and 76 at the high exposure values. These artifacts are due to the digitization of the film in the very opaque zones. This is not inconvenient since they are located outside the zone of practical interest of the film.

The statistical operations are all carried out by a processor 35 of the computer 35-37. This computer has a memory 36 in which it is possible to store the images delivered by the converter 9 as well as, at least temporarily, the working images prepared during the processing operation, the cloud 30 and the curve 17. The computer also has a program memory 37 containing the sequence of instructions enabling the performance of the processing operations mentioned hitherto. The processor 35 may also manage the converter 9 and the display monitor 38 on which the above-mentioned microcalcifications 10 and 11 can be made to appear in fine outline. A bus, not shown, enables the processor 35 to direct all the operations, from the illumination of the radiograph 6 up to the display on the monitor 38.

We shall now take a brief look at the preferred filtering operations implemented in the invention in order to prepare the signal 28. FIG. 8 shows image dots such as 40 to 50 of the radiograph 6. This image dots are scrutinized by the photoreceiver 8 and the signal prepared by the photoreceiver 8 is then sampled by the converter 9 which gives each of these image dots the values of measured optical density. The filtering carried out in the median filter 241 makes it possible to prepare the image of optical density filtered in a median way by processing the optical densities of N×N (where N is preferably an odd number) image dots contained in a sliding window 51. In the example described, the size of the window is 3×3. The result of this processing operation is assigned to the image dot 52 located at the center of this sliding window 51.

As for the filtering 68 and the subtraction 67, these operations may consist of a so-called top-hat filtering 76 comprising a closure in the sense of the transformations of mathematical morphology. This closure is followed by the subtraction. This closure comprises an expansion followed by an erosion, both preferably with the same structuring element: a 9×9 pixel window for example. Preferably, however, in the invention, a special top-hat filtering known as a filtering by numerical reconstruction is carried out. In this special filtering, the erosion is done iteratively by applying it, for a following erosion, to the results of a previous erosion. This operation is reiterated until the image may be considered to be no longer changing from one iteration to the next one. The value of this transformation with digital reconstruction, then, is that it leads to a far better detection of the highly contrasted objects than is the case with the normal top-hat transformation. These special transformations are described, in particular, by M. Coster and J. L. Chermant in *Precis d'analyse d'image* (A Summary of Image Analysis), Presses du CNRS, 1988.

The 9×9 pixel window enables the selection of microcalcifications of a given size. Since the microcalcifications are of different sizes, the correction computation 69 is applied, for example, three times. It is applied, firstly, with a filtering window 68 equal to 9×9, secondly with a 15×15 window and thirdly with a 27×27 window. It can be shown that, with these three images, the entire possible range of sizes of microcalcifications is covered.

What is claimed is:

1. A method to correct the measurement of the values of optical density of an image revealed on a radiographic film, the method comprising:
   a. measuring a value of optical density for each dot on the film, said measurement leading to a signal of optical density of the radiographed image;
   b. correcting said signal of optical density by taking into account non-linearities in the sensitivity of the radiographic film; and
   c. carrying out a top-hat transformation on said signal of optical density using a given size of structuring element on said signal of optical density.

2. A method according to claim 1, further comprising the steps of estimating for each level of optical density the slope of the characteristic curve of the transfer function made by the film, said characteristic curve establishing the correspondence between the radiographic exposure that the film has received and the optical density resulting therefrom;
   preparing a map of the slopes of said characteristic curve dot-by-dot of the film and assigning to each dot of the image a slope value of said curve, the slope value being a function of said curve and of the value of optical density at that particular dot; and
   correcting the measurement of optical density at each dot as a function of the value of optical density and of the slope of said characteristic curve at each dot.

3. A method according to claim 2, further comprising the steps
   a. preparing an estimator of noise of the optical density signal for each level of optical density;
   b. deducing the slope of said characteristic curve from said estimator.

4. A method according to claim 3, further comprising the steps of preparing said estimator by computing for each image dot the absolute value of the difference between said signal of optical density of the radiographic image and the result of a spatial filtering of said signal.

5. A method according to claim 4 further comprising the steps of:
   a. performing a spatial filtering of said signal of optical density of the radiographic image with a medium filter;
   b. said median filter assigning, to each chosen image dot, a value of optical density that corresponds to any order N value, once 2N+1 values of optical density, for 2N+1 dots located about the chosen dot and including it, have been chosen and arranged in rising order of values.

6. A method according to claim 3, further comprising the steps of:
   a. preparing said estimator for each level of optical density by searching for the mean of the values of optical density of the image dots belonging to a neighborhood (20×20) and assigning said mean of the values to the dot located at the center of this neighborhood as a new value of optical density.
   b. preparing a histogram with dual inputs of said new value of optical density and a noise estimator corresponding to the same dot.

7. A method according to claim 5, further comprising the steps of:
   a. assessing said characteristic curve by searching each level of optical density for the value of a most-represented noise; and
   b. filtering said most represented value as a function of the level of optical density.

8. A method according to claim 3, further comprising the steps of deducing the slope of said characteristic curve by subtracting a constant from the value of said estimator.

9. A method according to claim 8, further comprising the steps of subtracting said constant by computing a linear regression on a set of values of said estimator corresponding to low values of optical density.

10. A method according to claim 1, further comprising the steps of reiterating the correction for another given size of said structuring element.

11. A method according to claim 1 further comprising the step of performing said top-hat transformation by numerical reconstruction.

12. A method according to claim 10 further comprising the step of performing said top-hat transformation by numerical reconstruction.

* * * * *